United States Patent
Sun et al.

(10) Patent No.: US 8,567,268 B2
(45) Date of Patent: Oct. 29, 2013

(54) ENVIRONMENTAL TESTING DEVICE

(75) Inventors: Zheng-Heng Sun, Taipei Hsien (TW); Xiao-Feng Ma, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 534 days.

(21) Appl. No.: 12/861,031

(22) Filed: Aug. 23, 2010

(65) Prior Publication Data

US 2011/0283808 A1 Nov. 24, 2011

(30) Foreign Application Priority Data

May 21, 2010 (CN) .......................... 2010 1 0178825

(51) Int. Cl.
*G01N 17/00* (2006.01)
(52) U.S. Cl.
CPC .................................... *G01N 17/002* (2013.01)
USPC ............ 73/865.6; 73/431; D23/370; D23/387
(58) Field of Classification Search
USPC ................. 73/431, 865.6; 454/237, 275, 345; D23/352, 376, 377, 386, 387, 390, 393, D23/412

See application file for complete search history.

(56) References Cited

U.S. PATENT DOCUMENTS

| | | | | |
|---|---|---|---|---|
| 5,307,018 A | * | 4/1994 | Gadgil ........................... | 324/537 |
| 5,502,998 A | * | 4/1996 | Miller et al. .................... | 73/1.06 |
| 5,767,423 A | * | 6/1998 | Camp et al. .................... | 73/865.6 |
| 5,988,003 A | * | 11/1999 | Zuk ................................ | 73/865.6 |
| 6,023,985 A | | 2/2000 | Fournier | |
| 6,113,262 A | * | 9/2000 | Purola et al. ..................... | 374/45 |
| 6,272,767 B1 | | 8/2001 | Botruff et al. | |
| 6,360,621 B1 | * | 3/2002 | Eldred et al. .................. | 73/865.6 |
| 8,393,234 B2 | * | 3/2013 | Haefner et al. .............. | 73/865.6 |
| 2007/0034026 A1 | * | 2/2007 | Maciver et al. .............. | 73/865.6 |
| 2007/0081891 A1 | * | 4/2007 | Oh ................................. | 415/151 |
| 2010/0154571 A1 | * | 6/2010 | Yun et al. ...................... | 73/865.6 |

* cited by examiner

*Primary Examiner* — David A Rogers
(74) *Attorney, Agent, or Firm* — Altis & Wispro Law Group, Inc.

(57) ABSTRACT

An environmental testing device includes a humidity control module, a temperature control module; and an air circulation module. The air circulation module includes an enclosure and a fan received in the enclosure. Two pairs of airflow openings are defined in the enclosure and form different airflow passages that allow air to flow along different directions in the environmental testing device.

14 Claims, 4 Drawing Sheets

ENVIRONMENTAL TESTING DEVICE

BACKGROUND

1. Technical Field

The present disclosure relates to an environmental testing device capable of performing environmental testing on electronic devices.

2. Description of Related Art

Many types of electronic devices undergo a series of environmental tests under various combinations of temperature, humidity, and other climatic conditions produced using environmental testing devices to insure product reliability and performance at extreme environmental conditions.

Referring to FIG. 4, a typical environmental testing device 100 has an air circulation module 102 mounted therein. A fan (not shown) is disposed in the air circulation module 102. The air circulation module 102 has an air inlet 104 and an air outlet 106. When the environmental testing device 100 performs environmental tests on electronic devices placed therein, the fan outputs air from the air outlet 106 and draws air into the air inlet 104 to accelerate airflow in the device 100. However, the fan in the air circulation module 102 outputs air along a single direction, and air temperatures may not be uniform throughout the device 100. That may decrease accuracy of the test results.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
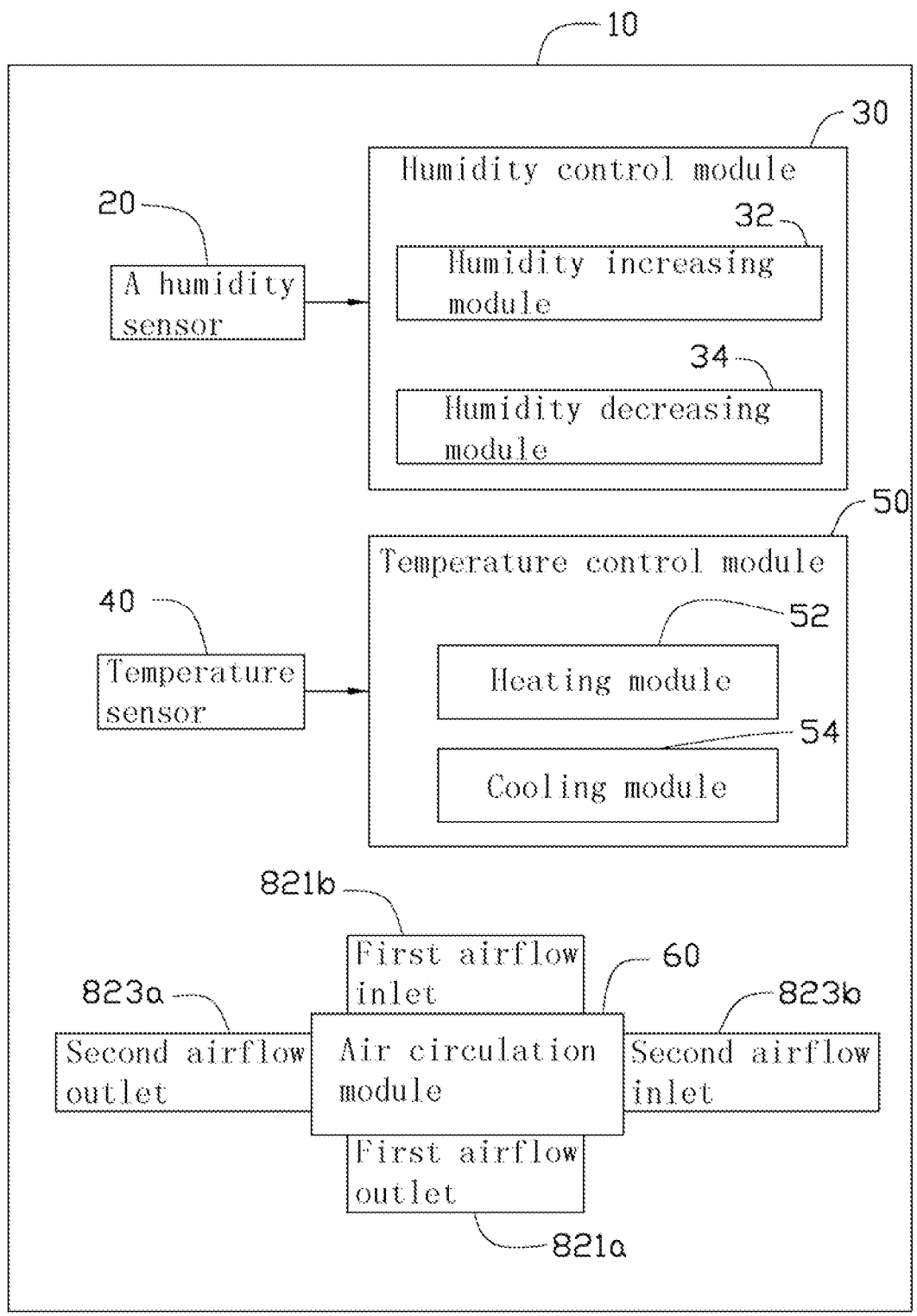
FIG. 1 is a block diagram of an environmental testing device according to an embodiment.

Referring to FIG. 1, an embodiment of an environmental testing device 10 includes a humidity sensor 20, a humidity control module 30 connected to the humidity sensor 20, a temperature sensor 40, a temperature control module 50 connected to the temperature sensor 40, and an air circulation module 60. The humidity control module 30 includes a humidity increasing module 32 and a humidity decreasing module 34. The temperature control module 50 includes a heating module 52 and a cooling module 54. The air circulation module 60 has a first airflow outlet 821a, a first airflow inlet 821b, a second airflow outlet 823a, and a second airflow inlet 823b.

Figure 2:
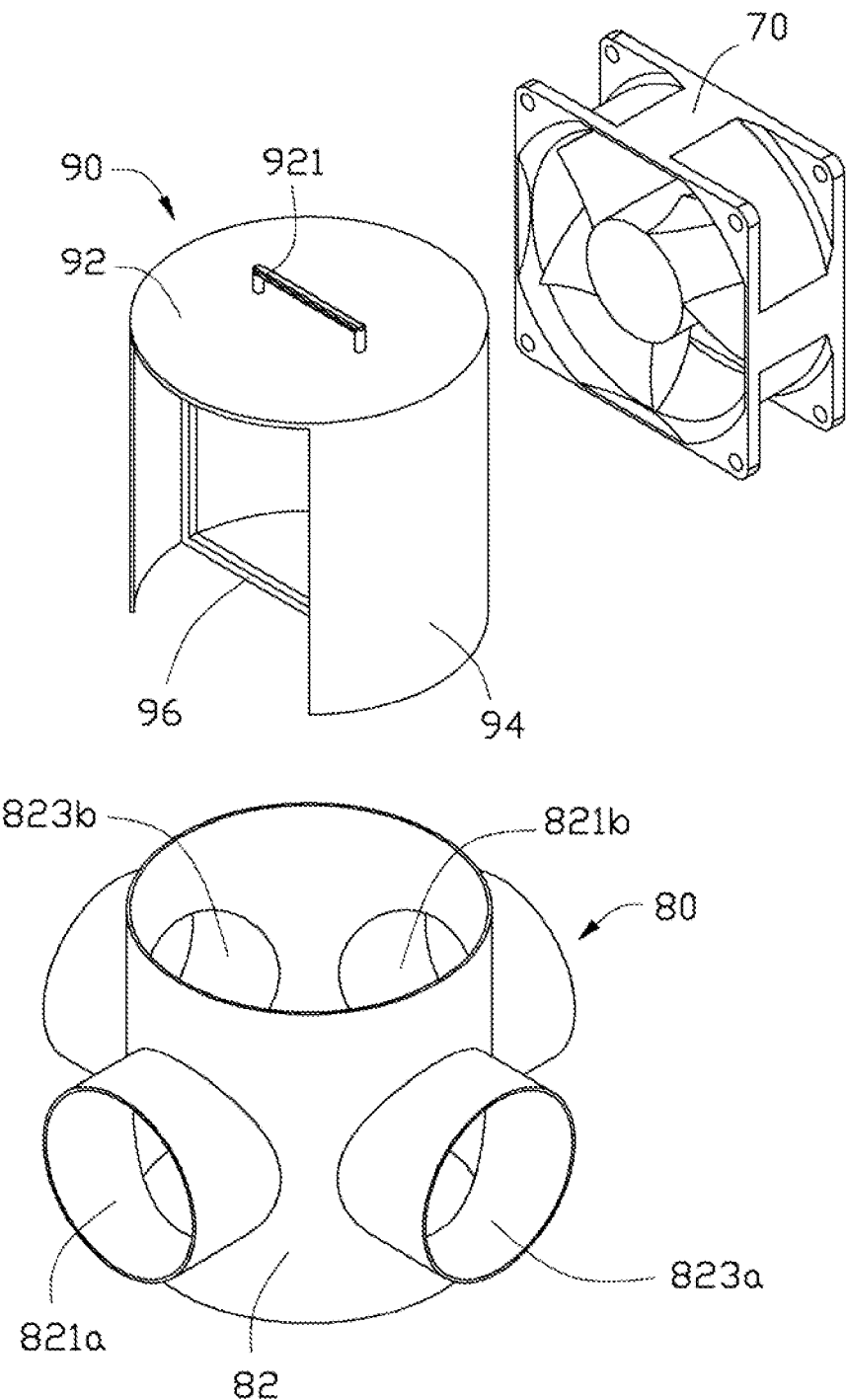
FIG. 2 is an exploded view of an air circulation module according to an embodiment.
Figure 3:
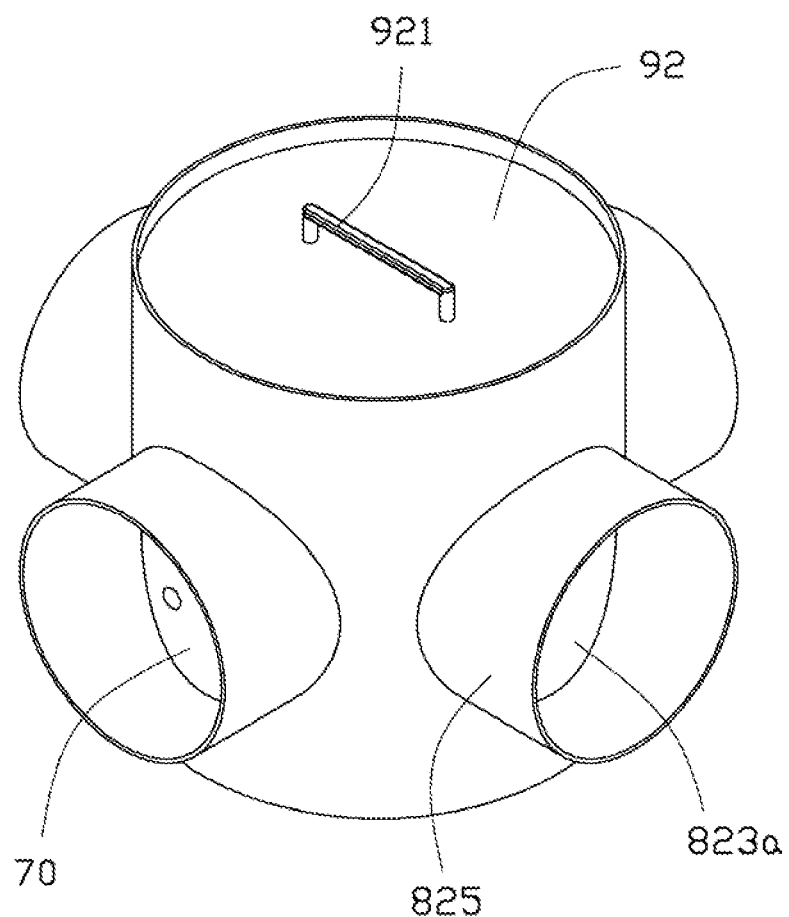
FIG. 3 is an assembled view of FIG. 2.
Figure 4:
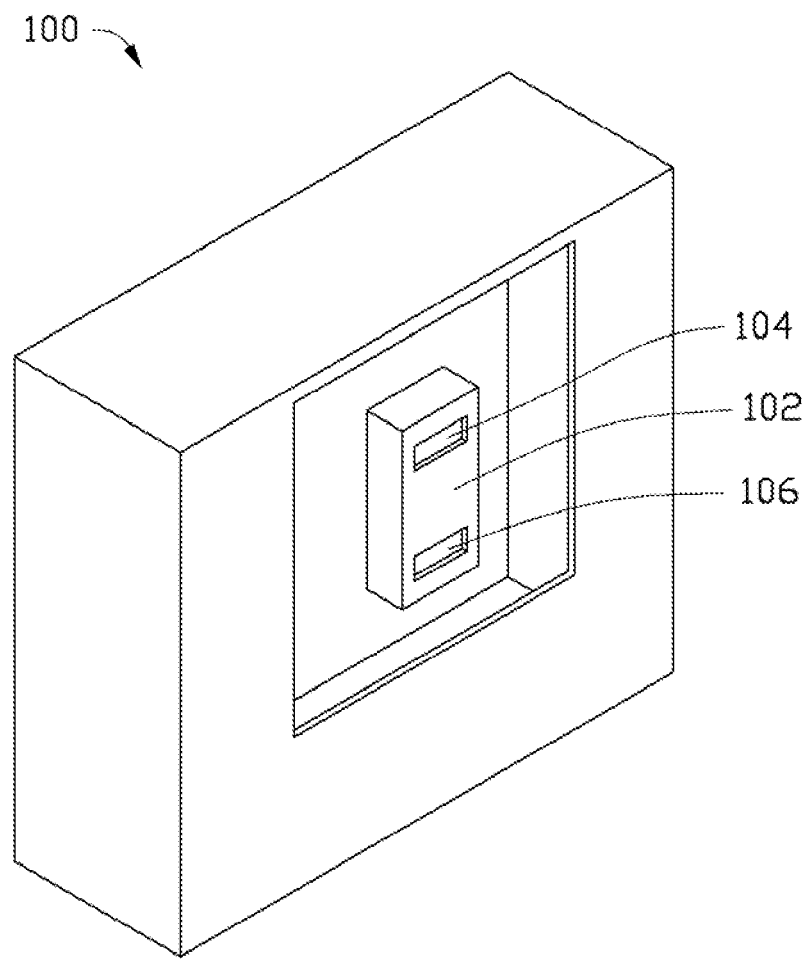
FIG. 4 illustrates a typical environmental testing device according to the prior art.

Referring to FIGS. 2 and 3, the air circulation module 60 includes a holding portion 80, a cover portion 90, and a fan 70 adapted to be accommodated in the holding portion 80. The holding portion 80 includes a hollow cylindrical main body 82. A base of the main body 82 is closed, and a top of the main body 82 is open.

The first airflow outlet 821a, the second airflow outlet 823a, the first airflow inlet 821b, and the second airflow inlet 823b are evenly defined in the side face of the main body 82. A circular airflow guide 825 protrudes an edge of each of the first airflow outlet 821a, the second airflow outlet 823a, the first airflow inlet 821b, and the second airflow inlet 823b.

The first air outlet 821a and the first air inlet 821b form a first airflow passage that allows air to flow along a first direction. The second air outlet 823a and the second air inlet 823b form a second airflow passage that allows air to flow along a second direction. The first direction is perpendicular to the second direction. An axis of the holding portion 80 is perpendicular to each of the first direction and the second direction.

The cover portion 90 includes a circular panel 92, a pair of arc-shaped side plates 94 extending down from the circular panel 92, and a mounting bracket 96 mounted between the side plates 94. A handle 921 is formed on the circular panel 92 of the cover portion 90.

In assembly of the air circulation module 60, the fan 70 is mounted in the mounting bracket 96 of the cover portion 90. The arc-shaped side plates 94 of the cover portion 90 are inserted in the holding portion 80 and abut an inner surface of the holding portion 80. The fan 70 mounted in the mounting bracket 96 of the cover portion 90 is received in the holding portion 80. Then the handle 921 of the cover portion 90 is rotated to adjust direction of the fan 70. In one embodiment, a front side of the fan 70 is located at the same side as the first air outlet 821a and the second air outlet 823a to output air through the first and second air outlets 821a, 823a. A rear side of the fan 70 is located at the same side as the first air inlet 821b and the second air inlet 823b for drawing in air from the first and second air inlet 821b, 823b.

To perform environmental testing on electronic devices (e.g. computer motherboards), the electronic devices are placed in the environmental testing device 10. The environmental testing device 10 is started. The humidity sensor 20 senses humidity in the environmental testing device 10 and informs the humidity control module 30. The humidity control module 30 compares the humidity with a predetermined humidity value. If the humidity in the environment testing device 10 exceeds the predetermined humidity value, the humidity decreasing module 34 is started to decrease the humidity in the environmental testing device 10. If the humidity in the environmental testing device 10 is less than the predetermined humidity value, the humidity increasing module 32 is started to increase the humidity in the environmental testing device 10. Thus, the environmental testing device 10 can produce the predetermined humidity condition.

The temperature sensor 40 senses the temperature in the environmental testing device 10 and informs the temperature control module 50. The temperature control module 50 compares the temperature with a predetermined temperature. If the temperature in the environmental testing device 10 exceeds the predetermined temperature, the cooling module 54 is started to decrease the temperature in the environmental testing device 10. If the temperature in the environmental testing device 10 is less than the predetermined temperature, the heating module 52 is started to increase the temperature in the environmental testing device 10. Thus, the environment testing device 10 can produce the predetermined temperature condition.

The fan 70 in the air circulation module 60 is started. The fan 70 draws in air from the first air inlets 821b and outputs air through the first air outlets 821a along the first airflow passage. The fan 70 also draws in air from the second air inlets 823b and outputs air through the second air outlets 823a along the second airflow passage. In one embodiment, air in the environmental testing device 10 flows along different directions. Air temperatures in the environmental testing device 10 are more even, which can increase accuracy of the test result.

It is to be understood, however, that even though numerous characteristics and advantages of the embodiments have been set forth in the foregoing description, together with details of the structure and function of the embodiments, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. An environmental testing device comprising:
   a humidity control module;
   a temperature control module; and
   an air circulation module comprising an enclosure, a fan received in the enclosure, and two pairs of airflow openings defined in the enclosure; and the two pairs of airflow openings defining two airflow channels that allow air to flow along different directions in the environmental testing device.

2. The environmental testing device of claim 1, wherein an axis of the enclosure is perpendicular to each of the airflow channels.

3. The environmental testing device of claim 1, wherein the enclosure comprises a cylindrical holding portion and a cover portion attached to the cylindrical holding portion, and the two pairs of airflow openings are defined in a side face of the cylindrical holding portion.

4. The environmental testing device of claim 3, wherein the cylindrical holding portion comprises a circular airflow guide protruding from an edge of each of the two pairs of airflow openings.

5. The environmental testing device of claim 3, wherein the cover portion comprises a circular panel and a pair of side plates extending from the circular panel, and the pair of side plates abut an inner surface of the cylindrical holding portion.

6. The environmental testing device of claim 5, wherein the cover portion further comprises a bracket mounted between the pair of side plates, and the fan is mounted in the bracket.

7. The environmental testing device of claim 6, wherein the fan is received in the cylindrical holding portion, and the circular panel of the cover portion is attached to a top of the cylindrical holding portion.

8. The environmental testing device of claim 7, wherein the cover portion is rotatable to adjust a direction of the fan.

9. An environmental testing device comprising:
   a humidity control module;
   a temperature control module; and
   an air circulation module comprising an enclosure and a fan received in the enclosure, the enclosure having a first pair of airflow openings and a second pair of airflow openings defined therein;
   wherein the first pair of airflow openings define a first airflow channel, and the second pair of airflow openings define a second airflow channel; wherein the first airflow channel is perpendicular to the second airflow channel.

10. The environmental testing device of claim 9, wherein the enclosure comprises a cylindrical holding portion and a cover portion attached to the cylindrical holding portion, and the first and second pairs of airflow openings are defined in a side face of the cylindrical holding portion.

11. The environmental testing device of claim 10, wherein the cover portion comprises a circular panel, a pair of side plates extend from the circular panel, and a bracket mounted between the pair of side plates, and the fan is mounted in the bracket.

12. The environmental testing device of claim 11, wherein the fan is received in the cylindrical holding portion, and the circular panel of the cover portion is attached to a top of the cylindrical holding portion.

13. The environmental testing device of claim 12, wherein the cover portion is rotatable to adjust a facing direction of the fan.

14. The environmental testing device of claim 13, wherein the first pair of airflow openings comprises a first airflow inlet and a first airflow outlet, the second pair of airflow openings comprises a second airflow inlet and a second airflow outlet, a front face of the fan is located at the same side as the first airflow outlet and the second airflow outlet, and a rear side of the fan is located at the same side as the first airflow inlet and the second airflow inlet.

* * * * *